United States Patent
Lauth et al.

(10) Patent No.: US 10,450,416 B2
(45) Date of Patent: Oct. 22, 2019

(54) NON ISOCYANATE POLYURETHANE FOAMS

(71) Applicants: FAURECIA INTERIEUR INDUSTRIE, Nanterre (FR); FAURECIA SIÈGES D'AUTOMOBILE, Nanterre (FR)

(72) Inventors: Marc Lauth, Strasbourg (FR); Rolf Mülhaupt, Freiburg (DE); Hannes Blattmann, Stegen (DE)

(73) Assignee: Faurecia Interieur Industrie, Nanterre (FR)

( * ) Notice: Subject to any disclaimer, the term of this patent is extended or adjusted under 35 U.S.C. 154(b) by 164 days.

(21) Appl. No.: 15/418,555

(22) Filed: Jan. 27, 2017

(65) Prior Publication Data

US 2017/0218124 A1    Aug. 3, 2017

(30) Foreign Application Priority Data

Jan. 29, 2016   (EP) ................... 16305097

(51) Int. Cl.
  *C08G 71/04* (2006.01)
  *C07D 317/36* (2006.01)
  *C08J 9/14* (2006.01)
  *C08G 101/00* (2006.01)

(52) U.S. Cl.
  CPC ........... *C08G 71/04* (2013.01); *C07D 317/36* (2013.01); *C08J 9/146* (2013.01); *C08G 2101/005* (2013.01); *C08G 2101/0008* (2013.01); *C08J 2203/142* (2013.01); *C08J 2205/044* (2013.01); *C08J 2205/06* (2013.01); *C08J 2375/04* (2013.01)

(58) Field of Classification Search
  CPC .............. C07D 317/36; C08G 71/04; C08G 2101/0008; C08G 2101/005; C08J 9/146; C08J 2203/142; C08J 2205/044; C08J 2205/06; C08J 2375/04
  See application file for complete search history.

(56) References Cited

U.S. PATENT DOCUMENTS

| | | | | |
|---|---|---|---|---|
| 5,340,889 A | * | 8/1994 | Crawford | C07C 269/04 525/523 |
| 2004/0192803 A1 | * | 9/2004 | Figovsky | C07D 303/32 521/178 |
| 2015/0024138 A1 | | 1/2015 | Figovsky et al. | |
| 2015/0183930 A1 | * | 7/2015 | Hsueh | C08G 71/04 523/400 |
| 2015/0247004 A1 | * | 9/2015 | Lombardo | C08G 71/04 528/371 |
| 2015/0299390 A1 | | 10/2015 | Michaud et al. | |
| 2016/0326132 A1 | * | 11/2016 | Cramail | C07D 317/38 |
| 2017/0260418 A1 | * | 9/2017 | Wu | B33Y 10/00 |

OTHER PUBLICATIONS

Cornille et al., "A new way of creating cellular polyurethane materials: NIPU foams", European Polymer Journal., vol. 66, May 1, 2015 (May 1, 2015), pp. 129-138.
Blattmann et al., "Flexible and Bio-based nonisocyanate polyurethane (NIPU) foams", Macromolecular Materials and Engineering, 2016, 9 pages.

* cited by examiner

*Primary Examiner* — John M Cooney
(74) *Attorney, Agent, or Firm* — Reising Ethington P.C.

(57) ABSTRACT

A curable isocyanate free formulation for preparing a polyurethane foam. The formulation includes a compound A chosen from multifunctional cyclic carbonates of a formula (I) or a mixture thereof, a compound B chosen from multifunctional cyclic carbonates containing oxyalkylene groups —OR3- of a formula (II) or a mixture thereof, a compound C chosen from multifunctional amines of a formula (III) or a mixture thereof and a compound D chosen from non-reactive blowing agents, as well as a process for preparing a non-isocyanate polyurethane foam, a foam obtainable by this process, compound B, a mixture of compounds A and B, the use of compound B for enhancing the solubility of a non-reactive blowing agent in a compound A and a foamable system having a first part A containing compound A and compound B and a second part B containing compound C, wherein part A and part B are preferably physically separated.

15 Claims, 3 Drawing Sheets

NON ISOCYANATE POLYURETHANE FOAMS

FIELD OF THE DISCLOSURE

The invention relates to non isocyanate polyurethane foams having good resilience and low density.

BACKGROUND OF THE DISCLOSURE

Polyurethanes are employed in a wide range of applications, notably in the form of foams. Depending on their composition, polyurethane foams can vary in structure from soft flexible foams used as cushioning materials to rigid foams used in insulating or structural materials.

Polyurethane foams are most often obtained by polymerization between a polyisocyanate and a hydroxyl terminated oligomer (polyol) in the presence of water. The reaction between polyol and isocyanate forms urethane linkages, while the reaction between polyisocyanate and water yields polyurea and gaseous carbon dioxide, the latter causing foaming of the composition.

Instead of water, other blowing agents may be used to perform expansion and foaming of the polymeric matrix. The blowing agent may be either produced in situ as a reaction product of the reactants (like water and isocyanate producing carbon dioxide). These blowing agents are called chemical blowing agents. Or the blowing agent may be a physical blowing agent, i.e. a non-reactive compound contained in the polymeric composition that is able to generate bubbles in the polymeric matrix during its formation, thereby leading to foam.

Polyurethane foams derived from polyisocyanates are associated with environmental issues because isocyanates raw materials, in particular methylene diphenyl 4,4'-diisocyanate (MDI) and toluene diisocyanate (TDI), the most widely used isocyanates in the polyurethane industry, and the corresponding aromatic diamines are classified as CMR (carcinogenic, mutagenic and reprotoxic substances).

Therefore, there is a need to produce polyurethane foams which are not derived from polyisocyanates, i.e. non isocyanate polyurethane foams (NIPU).

Cornille et al. ("A new way of creating cellular polyurethane materials: NIPU foams", European Polymer Journal, 66 (2015) 129-138) teaches the synthesis of polyurethane foams by reacting a tri- and difunctional mixture of five-membered cyclic carbonates with diamines to yield NIPU foams. The mixture of carbonates comprises a trifunctional carbonate (trimethylolpropane tris carbonate (TMP-Tri-C5)) and a difunctional carbonate (polypropylene oxide bis-carbonate (PPO-Bis-C5)). A poly(methylhydrogenosiloxane) is used as a chemical blowing agent to foam the NIPU by reaction with the diamines.

However, the synthesis described in this article suffers from important shortcomings from an industrial perspective. Indeed, the chemical blowing agent generates the release of hydrogen which is very flammable and thus risky and complicated to handle on an industrial scale. Furthermore, since the blowing agent is incorporated into the backbone of the polymer, there are limitations regarding maximal content of the blowing agent, thus limitations regarding foam properties, density and mechanical properties of the final product. The synthesis described in this article only enables the preparation of high density foams with apparent densities ranging from 194 to 295 kg/m$^3$. In this respect, the article teaches that the use of only tri-functional cyclic carbonate increases the apparent density of foams.

Therefore, there is still a need to develop a process making it possible to prepare NIPU foams that is easy to implement on an industrial scale, without the generation of flammable and explosive gas, and that also enables the preparation not only of high density flexible NIPU foams but also low density flexible NIPU foams.

The inventors of the present invention have succeeded in synthesizing NIPU foams meeting all these needs by reacting a multifunctional amine with multifunctional cyclic carbonates and alkoxylated derivatives thereof and by using a non-reactive blowing agent.

The NIPU foams of the invention have the advantage that they can be prepared in whole or in significant part from renewable domestic agricultural materials and thus qualify as biobased products.

SUMMARY OF THE INVENTION

One object of the invention is to provide a curable isocyanate free formulation for preparing polyurethane foam comprising the following compounds:

Compound A chosen from multifunctional cyclic carbonates of formula (I) or a mixture thereof:

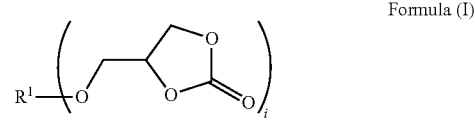

Formula (I)

wherein:
  i is an integer higher than or equal to 1, in particular from 1 to 10,
  $R^1$ is a linear or branched hydrocarbon chain one or several carbon atoms of which may be replaced with an heteroatom, a cycloalkyl, an heterocycle, an aryl or an heteroaryl, said hydrocarbon chain having at least 3 carbon atoms, in particular from 3 to 60 carbon atoms, Compound B chosen from multifunctional cyclic carbonates containing oxyalkylene groups —$OR^3$— of formula (II) or a mixture thereof:

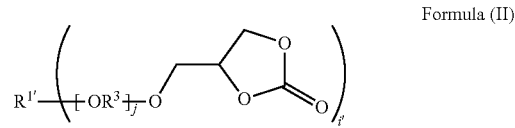

Formula (II)

wherein:
  i' is an integer higher than or equal to 1, in particular from 1 to 10,
  $R^{1'}$ is a linear or branched hydrocarbon chain one or several carbon atoms of which may be replaced with an heteroatom, a cycloalkyl, an heterocycle, an aryl or an heteroaryl, said hydrocarbon chain having at least 3 carbon atoms, in particular from 3 to 60 carbon atoms,
  j is an integer from 1 to 10,
  $R^3$ is a linear or branched hydrocarbon chain having at least one carbon atom, in particular from 2 to 6 carbon atoms, Compound C chosen from multifunctional amines of formula (III) or a mixture thereof:

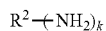  Formula (III)

wherein:
k is an integer higher than or equal to 2, in particular from 2 to 6,
$R^2$ is a linear or branched hydrocarbon chain one or several carbon atoms of which may be replaced with an heteroatom, a cycloalkyl or an heterocycle, said hydrocarbon chain having at least 2 carbon atoms, in particular from 2 to 60 carbon atoms, more particularly from 2 to 20 carbon atoms, even more particularly from 2 to 15 carbon atoms, Compound D chosen from non-reactive blowing agents.

One further object of the invention is a process for preparing a non-isocyanate polyurethane foam comprising the steps of:
reacting compounds A and B with compound C in the presence of compound D and a catalyst (compound E) so as to form an expanded reaction mixture,
curing said expanded reaction mixture so as to form a flexible non-isocyanate polyurethane foam,
wherein compounds A, B, C and D are as defined previously.

One further object of the invention is a non-isocyanate polyurethane foam obtainable by this process.

One further object of the invention is compound B as defined above.

One further object of the invention is a carbonate mixture comprising compound A and compound B as defined above.

One further object of the invention is a foamable system comprising the carbonate mixture (compounds A and B) and the multifunctional amines of formula (III) (compound C) as defined above in separate parts (physically separated).

One further object of the invention is the use of a compound B as defined above for enhancing the solubility of a non-reactive blowing agent in a compound A as defined above.

DETAILED DESCRIPTION

In the following description, the expressions "isocyanate free" and "non-isocyanate" refer to compositions which are not prepared from polyisocyanates.

The term "heteroatom" denotes an atom selected from N, O and S(O)n (where n is an 0, 1 or 2).

The term "cycloalkyl" denotes a monovalent or bivalent 3 to 8 membered carbon ring, for example cyclopropyl, cyclobutyl, cyclopentyl, cyclohexyl, cycloheptyl or cyclooctyl.

The term "heterocycle" denotes monovalent or bivalent non-aromatic mono- or bi-cyclic radical of four to nine ring atoms in which one to three ring atoms are heteroatoms independently selected from N, O and S(O)n (where n is 0, 1 or 2), with the remaining ring atoms being C. Particular is piperidyl or a cyclic carbonate.

The term "aryl" denotes a monovalent or bivalent aromatic carbocyclic group containing 6 to 14, particularly 6 to 10, carbon atoms and having at least one aromatic ring or multiple condensed rings in which at least one ring is aromatic. Examples include phenyl, benzyl, naphthyl, biphenyl, anthryl, azalenyl or indanyl.

The term "heteroaryl" denotes a monovalent or bivalent cyclic aromatic group containing 1, 2 or 3 heteroatoms, having at least one aromatic ring or multiple condensed rings in which at least one ring is aromatic. The aromatic ring may be a 6 membered ring, such as pyridinyl, or a 5-membered ring, such has thiazolyl, isoxazolyl, isothiazolyl, oxadiazolyl or thiadiazolyl.

According to an aspect of the invention, NIPU foam is synthesized by reacting a carbonate mixture (compounds A and B, which are different compounds) with an aliphatic multifunctional amine (compound C) that forms a polymer backbone, said reaction being performed with a catalyst (compound E) if necessary. A non-reactive blowing agent is also used as compound D to produce a cellular structure.

The carbonate mixture used in the invention is composed of a mixture of multifunctional five-membered cyclic carbonates of formula (I) (compound A) and of formula (II) (compound B) as described below. This mixture is advantageously devoid of any difunctional five-membered cyclic carbonates.

Accordingly, one object of the invention is a curable isocyanate free formulation for preparing a flexible polyurethane foam comprising:
compound A,
compound B,
compound C, and
compound D.

The curable formulation of the invention is liquid at ambient temperature (20° C.).

Preferably, the viscosity of the curable formulation of the invention is lower than or equal to 10 000 mPa·s at 50° C., preferably lower than 5 000 mPa·s at 50° C. as measured with an oscillatory rheometer, with oscillatory frequency sweep at 20, 50, 80° C., 5% deformation, 100-0.1 rad s$^{-1}$.

Compound A is chosen from multifunctional cyclic carbonates of formula (I) or a mixture thereof:

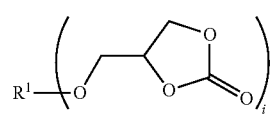  Formula (I)

wherein:
i is an integer higher than or equal to 1, in particular from 1 to 10, i.e. 1, 2, 3, 4, 5, 6, 7, 8, 9 or 10,
$R^1$ is a linear or branched hydrocarbon chain one or several carbon atoms of which may be replaced with an heteroatom, a cycloalkyl, an heterocycle, an aryl or an heteroaryl, said hydrocarbon chain having at least 3 carbon atoms, in particular from 3 to 60 carbon atoms.

In one embodiment, $R^1$ is an aliphatic hydrocarbon chain.

In one embodiment, compound A is a polyol, wherein i alcohol functions are replaced by a glycidylether carbonate group:

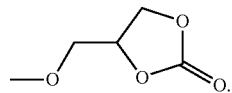

According to an aspect of the invention, a polyol is a compound comprising at least 2 alcohol functions. The polyol is free of any group which may interfere with the polymerization, in particular strong electrophilic groups such as ester groups or acid groups.

Compound A may be prepared from polyols by converting all or part of the alcohol functions of said polyol into glycidylether functions (see process details below), followed by carbonation of said glycidylether functions. Depending on the conversion rate of the alcohol functions, $R^1$ may contain one or several hydroxyl groups. $R^1$ may also contain one or several other groups, depending on the polyol from which compound A is prepared. Of course, the presence of these substituents on R', including the hydroxyl groups, must not interfere with the polymerization of the formulation.

In practice, compound A will be most often a mixture of compounds of formula (I) having the same $R^1$ but different values of i.

In one embodiment, compound A is a mixture of compounds of formula (I) having different $R^1$ and different values of i.

In one embodiment, i is an integer from 2 to 6, i.e. 2, 3, 4, 5 or 6, more particularly from 2 to 3.

In one embodiment, i is an integer higher than or equal to 3.

In one embodiment, $R^1$ is a linear or branched hydrocarbon chain having from 3 to 10 carbon atoms, i.e. 3, 4, 5, 6, 7, 8, 9 or 10 atoms, more particularly from 3 to 6 carbon atoms. For instance, the polyol from which compound of formula (I) is prepared may be chosen from the following groups:

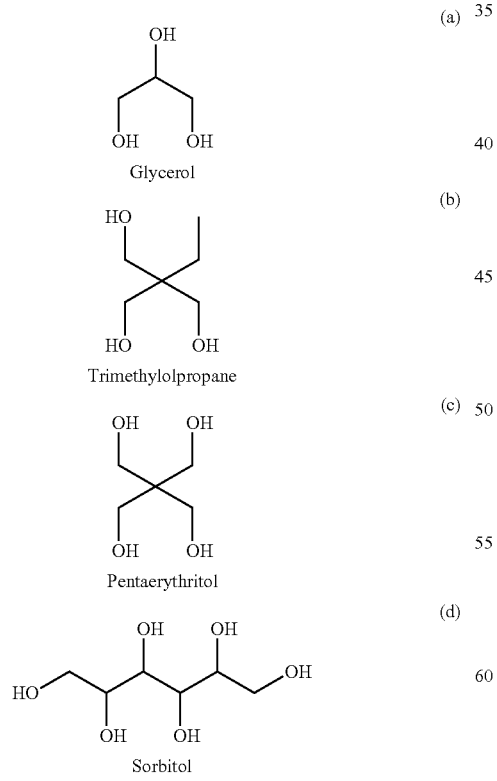

(a) Glycerol
(b) Trimethylolpropane
(c) Pentaerythritol
(d) Sorbitol

In a preferred embodiment, compound A is a trimethylolpropaneglycidylether carbonate of formula (Ia):

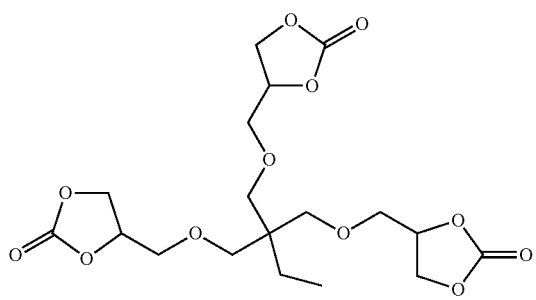 [SMILES: CCC(COCC1COC(=O)O1)(COCC1COC(=O)O1)COCC1COC(=O)O1]

Trimethylolpropaneglycidylether carbonate is commercially available from Specific Polymers under the trade name TMP-Tri-$C_5$. The average number of glycidylether carbonate groups in TMP-Tri-$C_5$ is 2.6. Average number of glycidylether carbonate groups can be determined for example by 1H and 13C NMR spectroscopy.

Compound A may also be a flexible plant-oil derived carbonate, in particular a carbonate bearing ester groups. Additionally, cyclic carbonates like Cardanol based derivatives may be also used such as cardanolglycidylether carbonate.

Compound B is chosen from multifunctional cyclic carbonates containing oxyalkylene groups —$OR^3$— of formula (II) or a mixture thereof:

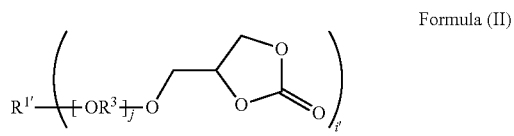

Formula (II)

wherein:
i' is an integer higher than or equal to 1, in particular from 1 to 10, i.e. 1, 2, 3, 4, 5, 6, 7, 8, 9 or 10,
$R^{1'}$ is a linear or branched hydrocarbon chain one or several carbon atoms of which may be replaced with an heteroatom, a cycloalkyl, an heterocycle, an aryl or an heteroaryl, said hydrocarbon chain having at least 3 carbon atoms, in particular from 3 to 60 carbon atoms,
j is an integer from 1 to 10, i.e. 1, 2, 3, 4, 5, 6, 7, 8, 9 or 10, in particular from 1 to 7, more particularly from 1 to 4,
$R^3$ is a linear or branched hydrocarbon chain having at least one carbon atom, in particular from 2 to 6 carbon atoms, i.e. 2, 3, 4, 5 or 6 carbon atoms.

In one embodiment, $R^{1'}$ is an aliphatic hydrocarbon chain.
In one embodiment, compound B is a polyol wherein i' alcohol functions are replaced by a glycidylether carbonate group containing j oxyalkylene groups —$R^3O$—:

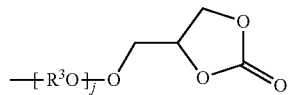

In practice, compound B will be most often a mixture of compounds of formula (II) having the same $R^{1'}$ but different values of i'.

In one embodiment, compound B is a mixture of compounds of formula (II) having different $R^{1'}$ and different values of i'.

Compound B may be prepared from alkoxylated polyols by converting the alcohol functions of said alkoxylated polyols into glycidylether functions (see process details below). Depending on the conversion rate of the alcohol functions, $R^{1'}$ may contain one or several hydroxyl groups. $R^{1'}$ may also contain one or several other groups depending on the polyol from which compound B is prepared. Of course, the presence of these substituents on $R^{1'}$, including the hydroxyl groups, must not interfere with the polymerization of the formulation.

In one embodiment, i' is an integer from 2 to 6, i.e. 2, 3, 4, 5 or 6, more particularly from 2 to 3.

In one embodiment, i' is an integer higher than or equal to 3.

In one embodiment, $R^{1'}$ is a linear or branched hydrocarbon chain having from 3 to 10 carbon atoms, i.e. 1, 2, 3, 4, 5, 6, 7, 8, 9 or 10 carbon atoms, more particularly from 3 to 6 carbon atoms. For instance, the polyol from which compound of formula (II) is prepared may be chosen from the above mentioned groups a), b), c) or d).

i and i' may be identical or different, preferably identical.

$R^1$ and $R^{1'}$ may be identical or different, preferably identical.

In one embodiment, $R^3$ is a linear or branched hydrocarbon chain having from 2 to 6 carbon atoms, i.e. 2, 3, 4, 5 or 6 carbon atoms, more particularly from 2 to 4 carbon atoms. $R^3$ may be for instance chosen from —$CH_2$—, —$CH_2$—$CH_2$—, —$CH(CH_3)$—$CH_2$—, —$CH_2$—$CH_2$—$CH_2$—, —$CH_2$—$CH_2$—$CH_2$—$CH_2$—, —$CH_2(CH_3)$—$CH_2$—$CH_2$—.

In a preferred embodiment, compound B is chosen from alcoxylated trimethylolpropaneglycidylether carbonates of formula (IIa) or a mixture thereof:

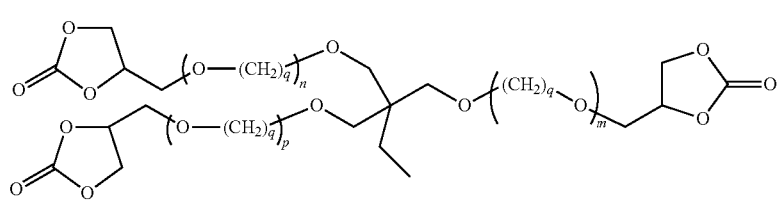

(IIa)

wherein:
q represents an integer higher than or equal to 1, in particular from 2 to 20, i.e. 1, 2, 3, 4, 5, 6, 7, 8, 9, 10, 11, 12, 13, 14, 15, 16, 17, 18, 19 or 20, preferably from 2 to 7 (thus 1, 2, 3, 4, 5, 6, 7 or 8), more preferably from 2 to 4, even more preferably equal to 2, and n, m and p, identical or different, represent integers from 1 to 20, i.e. 1, 2, 3, 4, 5, 6, 7, 8, 9, 10, 11, 12, 13, 14, 15, 16, 17, 18, 19 or 20, preferably from 1 to 10 (thus 1, 2, 3, 4, 5, 6, 7, 8, 9 or 10).

In one particular embodiment, q=2 or 3.

In one particular embodiment, q=2 or 3 and n, m and p, identical or different, are equal to 1, 2, 3, 4, 5, 6 or 7.

In one embodiment, compound B is not Laprolat® L-803 marketed by Macromer Co,

Russia, i.e. the following polyoxypropylated trimethylol propane with cyclocarbonate terminal:

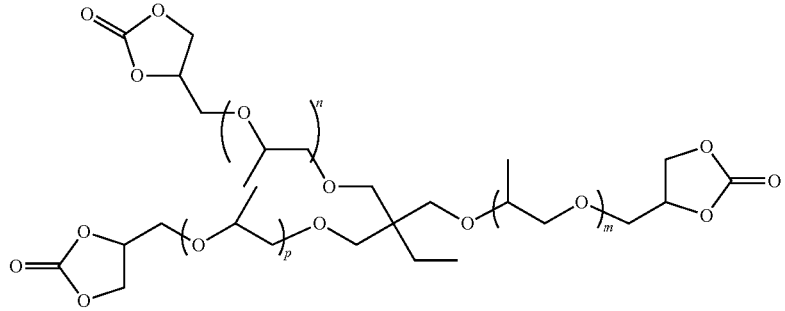

n + m + p = 9

In a preferred embodiment, compound B is chosen from alcoxylated trimethylolpropaneglycidylether carbonates of formula (IIb) or a mixture thereof:

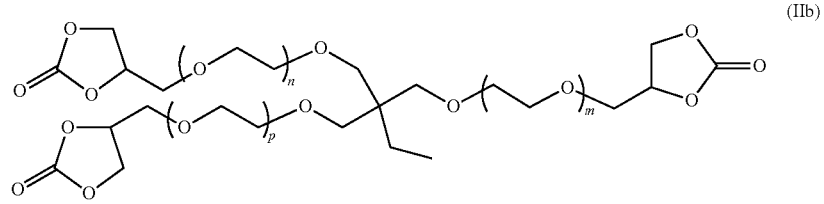

(IIb)

wherein n, m and p, identical or different, is equal to 1, 2, 3, 4, 5, 6, 7, 8, 9 or 10, preferably are equal to 1, 2, 3, 4, 5, 6, 7 or 8, more preferably equal to 6 or 7.

In one particular embodiment, n+m+p=19 or 20.

In one particular embodiment, n=m=p=6 or 7.

Compound B may be prepared from flexible plant-oil derived carbonates, in particular carbonates bearing ester groups. Additionally, cyclic carbonates like Cardanol based derivatives may be also used such as cardanolglycidylether carbonate to prepare compound B.

One object of the invention is a compound B as defined previously, in particular an alcoxylated trimethylolpropaneglycidylether carbonate of formula (II) as defined previously, more particularly an alcoxylated trimethylolpropaneglycidylether carbonate of formula (IIa) or of formula (IIb) as defined previously.

An advantage of compounds A is that they can be easily prepared in large scale or by reacting a polyol (which is either commercially available or obtainable from renewable resources such as sorbitol, sucrose, pentaerythritol, glycerol or trimethylolpropane) with epichlorohydrin (see for instance WO01/60901), followed by a carbonation reaction for instance with 10 bar $CO_2$ pressure, 1 wt.-% TBAB at 140° C. within 4 days. Any polyol can be used, in particular any sugar alcohol. The degree of conversion of the alcohol functions of the polyol (value i) depends on the accessibility of the alcohol functions. Primary alcohol functions are more easily accessible and thus more reactive than secondary or tertiary alcohols. Therefore, it is more likely to achieve full conversion of all alcohol groups with a polyol containing only primary alcohol functions than with a polyol containing secondary or tertiary alcohol functions. If the degree of conversion of the alcohol functions of the polyol is lower than 100%, the synthesis leads to a mixture of carbonates of formula (I) wherein $R^1$ is substituted or with hydroxyl groups. Trimethylolpropaneglycidylether carbonate (also known as trimethylolpropane tris carbonate or TMP-Tri-C5) can be prepared for instance by carbonation of commercially available trimethylolpropane triglycidylether (see Fleischer, Blattmann, Mülhaupt, Green Chemistry, 2013, 15, 934-942).

Compound B can also be prepared by reacting polyols (which are either commercially available or obtainable from renewable resources such as sorbitol, sucrose, pentaerythritol, glycerol or trimethylolpropane) with a cyclic ether (such as epoxide or oxetan) to form the corresponding alkoxylated polyol (see for instance WO2012/074027). Then, the alkoxylated polyol can be reacted with epichlorohydrin, followed by a carbonation reaction as described above. Any polyol can be used, in particular any sugar alcohols. Accordingly, j oxyalkylene groups —$OR^3$— (formula (II)) or —$O(CH_2)q$- (formula (IIa)) are inserted in each branch terminated with a cyclic carbonate. The degree of conversion of the alcohol functions into glycidyl ether carbonate groups depend on the accessibility of the alcohol functions. Primary alcohol functions are more easily accessible and thus more reactive than secondary or tertiary alcohols. Therefore, it is more likely to achieve full conversion of all alcohol groups with a polyol containing only primary alcohol functions than with a polyol containing secondary or tertiary alcohol functions. Furthermore, the number j, n, m and p of inserted oxyalkylene groups may differ between each branch terminated with a cyclic carbonate. In that case, the synthesis leads to a mixture of carbonates of formula (II) or (IIa) wherein j, n, m and p are each different.

FIG. 5 shows the synthesis of ethoxylated trimethylolpropaneglycidylether carbonate of formula (IIb).

Combining compound A with compound B makes it possible to obtain a blend of carbonates having a viscosity lower than the viscosity of compound A. The viscosity is important as regards to the miscibility, the homogeneity, the time of mixing and the solubility of the blowing agent within the polymer composition.

Thus, one further object of the invention is a carbonate mixture comprising compound A as defined above and compound B as defined above.

Preferably, the viscosity of the carbonate mixture (compound A and compound B) is:
from 1 to 10 Pa·s at 50° C., preferably from 1 to 5 Pa·s at 50° C., more preferably from 1 to 3 Pa·s at 50° C.;
from 1 to 320 Pa·s at 20° C., preferably from 4 to 90 Pa·s at 20° C., more preferably from 10 to 29 Pa·s at 20° C.

Viscosity is measured with an oscillatory rheometer, with oscillatory frequency sweep at 20, 50, 80° C., 5% deformation, 100-0.1 rad $s^{-1}$.

Compound B also makes it possible to improve the solubility of the blowing agent in the polymeric reaction mixture, in particular when the blowing agent is a hydrofluorocarbon, such as SOLKANE® 365/227 blends.

Accordingly, one further object of the invention is the use of a compound B as defined previously for enhancing the solubility of a non-reactive blowing agent in a compound A as defined previously.

One further object of the invention is a method for enhancing the solubility of a non-reactive blowing agent in a compound A as defined previously, wherein said method comprises the step of mixing compound B as defined as defined previously with compound A so as to form a polymeric blend and then mixing said non-reactive blowing agent (compound D) with said polymeric blend.

In one embodiment, compound C is mixed with the polymeric blend prior to mixing the non-reactive blowing agent with said polymeric blend.

The weight ratio of compound A over compound B can be from 20/80 to 80/20, in particular from 50/50 to 70/30, more particularly around 60/40.

Compounds A and B with long chain segments and/or a low number of carbonate functionalities (such as trimethylolpropaneglycidylether carbonate or ethoxylated trimethylolpropaneglycidylether carbonate of formula (IIb)) will yield to flexible foams, while Compounds A and B with short chain segments and/or a high number of carbonate functionalities will yield to rigid foams.

Compound C is chosen from multifunctional amines of formula (III) or a mixture thereof:

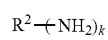

Formula (III)

wherein:
- k is an integer higher than or equal to 2, in particular from 2 to 6,
- $R^2$ is a linear or branched hydrocarbon chain one or several carbon atoms of which may be replaced with an heteroatom, a cycloalkyl or an heterocycle, said hydrocarbon chain having at least 2 carbon atoms, in particular from 2 to 60 carbon atoms more particularly from 2 to 20 carbon atoms, even more particularly from 2 to 15 carbon atoms.

Compound C is used as a hardener by reacting with cyclic carbonate groups of compounds A and B, thereby cross-linking the cyclic carbonate terminated chains one to each other.

The multifunctional amine of formula (III) can be chosen among amines which are classically used for epoxy cured, for instance from diamines, in particular linear aliphatic diamines, such as 1,2-diamonethane, 1,3-diaminopropane, butane-1,4-diamine, pentane-1,5-diamine, 1,6-diaminohexane, or 1,12 diaminododecane, or cyclic aliphatic diamines, such as isophorondiamine (IPDA), triamines, or any other polyamines, such as polyethylene imine (e.g. Lupasol® FG from BASF) or dimeric fatty acid diamines such as Priamine® 1074 from Croda, or Jeffamine® from Huntsman Petrochemical, LLC.

Amines with long chain segments and/or a low number of functionalities —$NH_2$ (such as Lupasol® FG and IPDA) will yield to flexible foams, while amines with short chain segments and/or a high number of functionalities —$NH_2$ yield to rigid foams (such as 1,6-diaminohexane or Priamine® 1074).

It is also possible to tailor the mechanical properties of the foam by using different ratios of amine and cyclic carbonate groups. For instance, by decreasing the ratio of amine groups over cyclic carbonate groups, the network density can be decreased, thereby leading to a decrease of Tg and stiffness. Conversely, by increasing the ratio of amine groups over cyclic carbonate groups, the network density can be increased, thereby leading to an increase of Tg and stiffness.

The blowing agent (compound D) creates holes in the polymeric matrix, thereby producing a cellular structure. According to the invention, the blowing agent is non-reactive, i.e. inert toward the polymeric matrix forming components (also known as physically active blowing agent). It is preferably liquid under normal conditions and has a boiling point below 100° C., preferably below 50° C., in particular in the range from −50° C. to 30° C., so that it vaporizes under the action of the exothermic polymerization reaction. It can be any gas releasing agent. Examples of such liquids are hydrocarbons such as n-pentane, isopentane and/or cyclopentane, ethers, or halogenated hydrocarbons, in particular fluorinated hydrocarbons, as long as they have no ozone depletion potential, nitriles, such as 2,2'-azobisisobutyronitrile, nitrogen or carbon dioxide, or mixtures thereof.

The blowing agent can be chosen in particular among liquid hydrofluorocarbon blends, such as SOLKANE® 365/227 blends, marketed by SOLVAY. The boiling point of SOLKANE® 365/227 blend is 30° C. In order to avoid the complete evaporation of SOLKANE before effective mixing with the polymeric reaction mixture, the temperature of this mixture should be in the range of about 20° C. to 25° C.

The catalyst (compound E) is used to increase the kinetics of the carbonate/amine reaction. A wide range of catalysts can be used (see for instance Blain et al., Green Chemistry 2014, 16, 4286). As non-limiting examples, it can be chosen from amine catalysts, such as triazabicyclodecene (TBD), 1,4-diazabicyclo[2.2.2]octane (DABCO), 1,8-diazabicyclo[5.4.0]undec-7-ene (DBU), trimethylhydroxyethyl ethylene diamine, trimethylaminopropylethanolamine, dimethylethanolamine, bis(2-dimethylaminoethyl) ether, triethylenediamine, dimethylaminocyclohexane, N-methyl morpholine, or organometallic catalysts such as stannous octoate, lead octoate, dibutyltin dilaurate, potassium acetate or potassium ethyl-hexoate, or mixtures thereof.

The amount of catalyst added to the carbonate mixture generally ranges from 0.1 wt % to 5 wt %, in particular from 0.5 wt % to 2 wt %, the percentage being expressed relative to the carbonate mixture (compound A and B).

A further object of the invention is a process for preparing a flexible non-isocyanate polyurethane foam comprising the steps of:
- reacting compounds A and B with compound C in the presence of compound D and compound E so as to form an expanded reaction mixture,
- curing said expanded reaction mixture so as to form a flexible non-isocyanate polyurethane foam,
- wherein compounds A, B and C are as defined previously.

According to the process of the invention, the carbonate mixture if formed by mixing compound A and compound B. This carbonate mixture is then mixed with the catalyst (compound E) and the multifunctional amine (compound C), so as to form a reaction mixture. The cyclic carbonate groups of the compounds A and B react with the cross-linking multifunctional amine, thus leading to the polymerization of said reaction mixture. Upon polymerization, the viscosity of the reaction mixture increases until it reaches the gelation point of the composition. Viscosity continues to increase after gelation point is reached. The gelation point of the composition can be determined by doing oscillatory rheological experiments, at a temperature of 80° C., a 5% deformation, 10 rad s$^{-1}$. Gelation point is determined by the crossover of storage G' and loss modulus G''.

The non-reactive blowing agent (compound D) is added to this polymeric reaction mixture before reaching the gelation point of the reaction mixture. Since the polymerization reaction is exothermic, the non-reactive blowing agent is preferably added the polymeric reaction mixture by maintaining the temperature of the reaction mixture in the range of 10 and 30° C., in particular from 20° C. to 25° C. in order to avoid the complete vaporization of the blowing agent before effective mixing with the polymeric reaction mixture. By changing from a liquid to a gas, the blowing agent generates the formation of bubbles within the polymer composition and causes its expansion, thereby leading to the production of a viscous foam. The degree of expansion of the foam can be controlled by adjusting the temperature of the polymer composition and the amount of blowing agent within the composition An optimal degree of expansion is obtained by adding the blowing agent to the reaction mixture just before reaching the gelation point of the polymeric composition.

The amount of blowing agent added to the reaction mixture generally ranges from 0 wt % to 100 wt %, in particular from 10 wt % to 70 wt %, more particularly from 10 to 30 wt.-%, the percentage being expressed relative to the weight of the reaction mixture.

The mixing of the ingredients can be performed using any suitable mixing equipment, including static mixing equipment, impingement mixing equipment, or other suitable mixing equipment. In small scale, external heating may be necessary to start the reaction. In large scale, external heating may not be necessary since the reaction is exothermic. The reaction mixture can heat up by itself to 60-90° C.

The expansion of the foam can be achieved within a relatively short time after the mixing of the blowing agent (between 0.5 to 20 minutes) with the polymer mixture and leads to a homogeneous foam. The pore sizes as measured by optical microscope are generally lower than 1 000 µm, in particular lower than or equal to 250 µm.

The expanded reaction mixture can be cured by heating until it is in tack-free state. Curing is generally performed in molds. Curing temperatures of up to 100° C. or more can be used, in particular from 50° C. to 100° C., more particularly from 70° C. to 80° C. Curing to a tack-free state generally takes place in a matter of a few hours (e.g. 14 h at 80° C.).

The reaction mixture may contain optional ingredients such plasticizers, fillers, colorants, preservatives, odor masking agents, flame retardants, smoke suppressants, thixotropic agents, mould release agents, surfactants, foam stabilizers, biocides, antioxidants, UV stabilizers, antistatic agents or foam cell nucleators.

One further object of the invention is a non-isocyanate polyurethane foam obtainable by this process.

The hardness of the foams of the invention can be from 5 kPa to 20 kPa, in particular from 8 kPa to 17 kPa. The load-bearing properties (hardness) of flexible foams are measured by simple compression mode on a small cut sample according to ISO 3386 standard (September 2010).

The resilience of the foams of the invention can be from 65% to 80%, in particular from 70% to 78%. The resilience is measured according to standard PV. 3427 (October 2010). The complete stress strain curve is recorded during the last cycle and the ratio of the area under the loading and the unloading curve is then used to measure the energy absorbed during compression. This ratio is called hysteresis and provides a simple measure of foam resilience (also named elasticity).

The hysteresis loss of the foams of the invention can be from 25% to 16%, in particular from 20% to 18%. The hysteresis loss is measured according to standard PV. 3427 (October 2010).

The process of the invention makes it possible to prepare flexible foams over a wide range of densities. The foam of the invention can be of high density (higher than 80 kg/m$^3$) or of low density (lower than or equal to 80 kg/m$^3$). The apparent density of the foam of the invention can be less 160 kg/m$^3$, in particular from 10 kg/m$^3$ to 80 kg/m$^3$ or from 80 kg/m$^3$ to 140 kg/m$^3$. Apparent density is measured according to ISO 845 standard (October 2009). A cut parallelepiped of foam is weighted and its dimensions are measured. The weight to volume ratio is expressed in kg/m$^3$.

Preferably, the foams of the invention have a glass transition temperature from −36° C. to 25° C.

One further object of the invention is a foamable system comprising the carbonate mixture (compounds A and B) and the aliphatic polyamine in separate parts (physically separated):

a first part A containing a carbonate mixture comprising:
  Compound A as defined above and
  Compound B as defined above, and
a second part B containing compound C as defined above,
part A and part B being physically separated.

In one embodiment, compounds A and B are physically separated within part A.

The advantage of this foamable system is that the two components (carbonates on one side and multifunctional amine on the other side) are physically separated, which prevents that they react together. The system can be stored until the moment at which the foam is prepared. One can easily prepare a foam by mixing the two parts together (without having to adjust the relative proportions of each reactant) in combination with a blowing agent and a catalyst if needed.

In one embodiment, the foamable system further comprises a catalyst (compound E) either in part A (i.e. mixed with compounds A and/or B) or in part B (i.e. mixed with compound C), or in a third part C physically separated from part A and part B.

In one embodiment, the foamable system further comprises a non-reactive blowing agent (compound D) either in part A (i.e. mixed with compounds A and/or B), in part B (i.e. mixed with the multifunctional amine) or in third part C (i.e. mixed with the catalyst), or in fourth part physically separated from part A, part B and part C.

The foamable system of the invention can be provided in the form of a ready-to-use kit-of-parts comprising all the necessary components for preparing the foam (i.e. compounds A, B, C and D).

The polyurethane foams of the present invention are useful in a wide variety of applications, in particular for insulating or damping elements, in vehicle construction, or for upholstery, or bedding. They have appropriate hardness, resilience (or hysteresis loss), which make them particularly suitable for seating applications in the automotive industry.

The invention is further illustrated but not limited by the following examples.

EXAMPLE 1

NIPU Foams According to the Invention Were Prepared as Described Below.

Reactants:
Trimethylolpropaneglycidylether carbonate of formula (Ia):

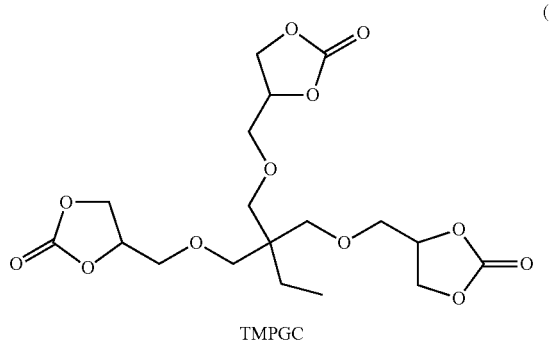

TMPGC (wherein the average number of glycidylether carbonate groups is 2.6)

Ethoxylated trimethylolpropaneglycidylether carbonate of formula (IIb):

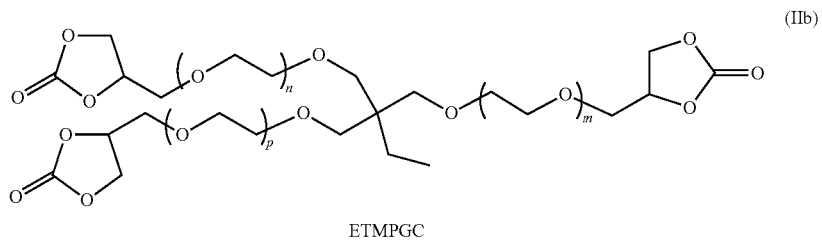

ETMPGC wherein n+m+p=19.2 and the average value of n, m, p is 6.4.

HMDA (1,6-diaminohexane).

Carbonate mixtures composed of TMPGC and ETMPGC were prepared by varying the amount of ETMPGC in the mixture. The influence of the amount of the ETMPGC on the gelation time of the carbonate mixture, and the Tg and Td of the foam was studied.

Figure 1:
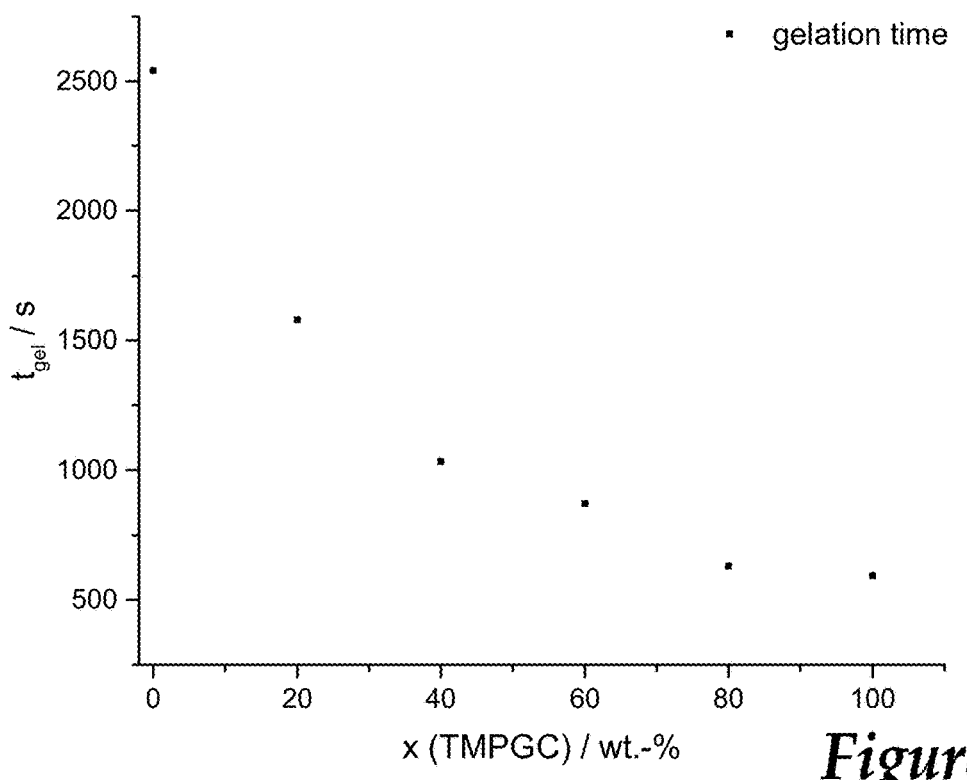
FIG. 1 shows the gelation time of the carbonate mixture when combined with HMDA at 80° C. as a function of the weight percentage of TMPGC in the carbonate mixture.

FIG. 1 shows the gelation time of the carbonate mixture when combined with HMDA at 80° C. as a function of the weight percentage of TMPGC in the carbonate mixture. The gelation time was determined by rheological oscillatory experiments using plate-plate geometry with 5% deformation and 10 rad s$^{-1}$. Gelation time was determined by the crossover of storage (G') and loss modulus (G'').

As it can be seen from FIG. 1, 100 wt % of TMPGC together with HMDA (TMPGC/HMDA=24 wt %) yielded a gelation time of 10 min compared to 42 min with 100 wt % of ETMPGC.

Based on visual and analytical (gelation times) inspection, a carbonate mixture comprising 60 wt % of TMPGC seems to be the most promising system regarding flexible mechanical properties and sufficient short gelation times (of about 14 min).

Figure 3:
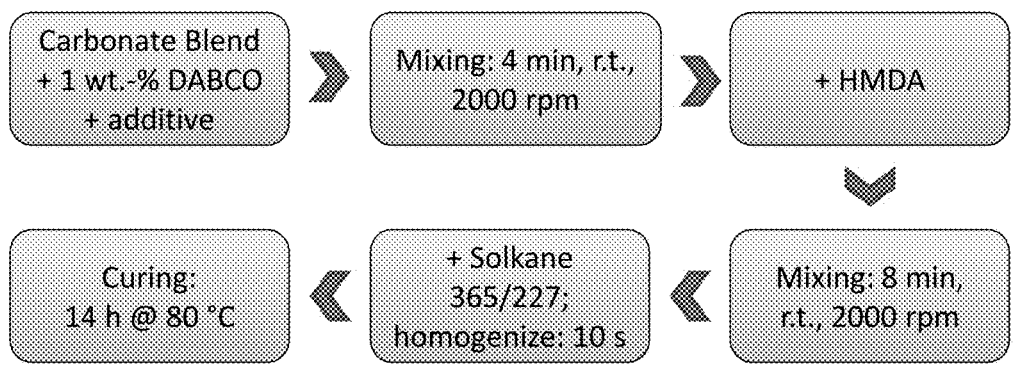
FIG. 3 shows a procedure for preparing a foam according to the invention (Example 1).

NIPU foams were prepared according to the procedure shown in FIG. 3. 1,4-Diazabicyclo[2.2.2]octane (DABCO, 1 wt.-% regarding carbonate mixture) was used as catalyst and Solkane® 365/227 as a blowing agent.

The carbonate mixture was mixed with DABCO using a KPG stirrer (2000 rpm) at room temperature for 4 min. After adding HMDA, the mixture was continuously stirred without additional heating. After 8 min, when a suitable increased viscosity was achieved and before reaching the gelation point, the blowing agent Solkane (25 wt.-%) was added. The mixture was homogenized for 10 s, poured into a PP cup (cup diameter 5.0 cm) and cured for 14 h at 80° C. The foaming process was completed during the first 30 min. The sample was prepared with a total mass of 17 g. Foam formation was excellent (homogeneous foam with a height of 5.5 cm). The pore size was in the range of 250 μm to 500 μm.

The glass-transition temperature Tg (squares) and the decomposition temperature Td (triangles) of the foam was determined according to the wt % of ETMPGC. Td was measured by thermogravimetric analysis under air (10 K·min$^{-1}$). Tg was measured by differential scanning calorimetry (heating and cooling rate 10 K·min$^{-1}$, second heating curve was analyzed). The results are summarized in table 1.

TABLE 1

| Sample | Amount of TMPGC (wt %) | Amount of ETMPGC (wt %) | Tg (° C.) | Td (° C.) | Td at 30% decomposition 100 (° C.) |
| --- | --- | --- | --- | --- | --- |
| 1 | 100 | 0 | 26.5 | 270 | 328 |
| 2 | 80 | 20 | 13.4 | 267 | 334 |
| 3 | 60 | 40 | 0.9 | 275 | 340 |
| 4 | 40 | 60 | −13 | 283 | 345 |
| 5 | 20 | 80 | −29.7 | 307 | 356 |
| 6 | 0 | 100 | −37 | 316 | 362 |

Figure 2:
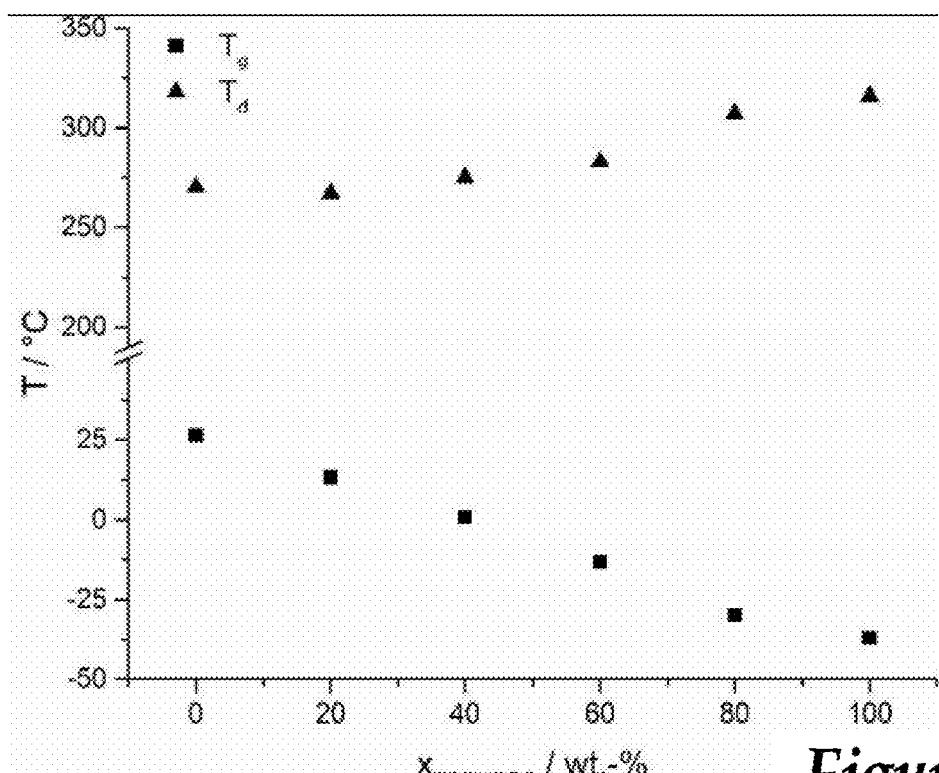
FIG. 2 shows the glass-transition temperature Tg (squares) and the decomposition temperature Td (triangles) of the foam as a function of the weight percentage of TMPGC in the carbonate mixture.

FIG. 2 shows as a function of the weight percentage of TMPGC in the carbonate mixture. Tg decreases as the amount of ETMPGC increases. Td increases as the amount of ETMPGC increases, therefore the thermal stability of the foam increases as the amount of ETMPGC increases.

EXAMPLE 2

Figure 4:
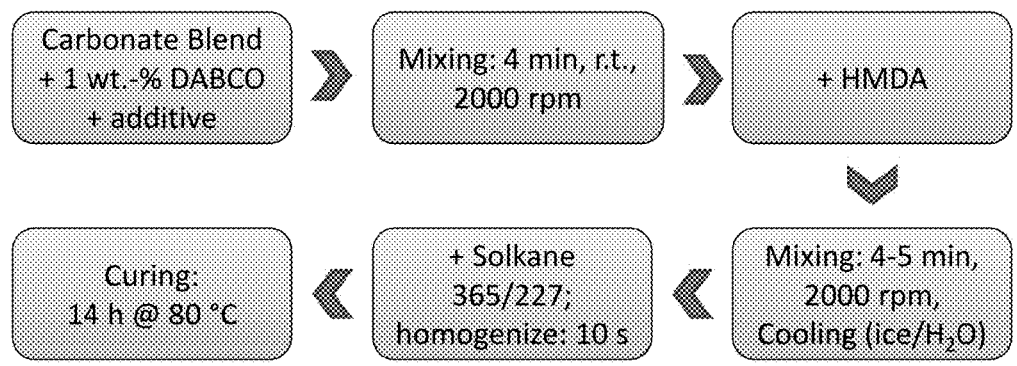
FIG. 4 shows a procedure for preparing a foam according to the invention (Example 2).
Figure 5:
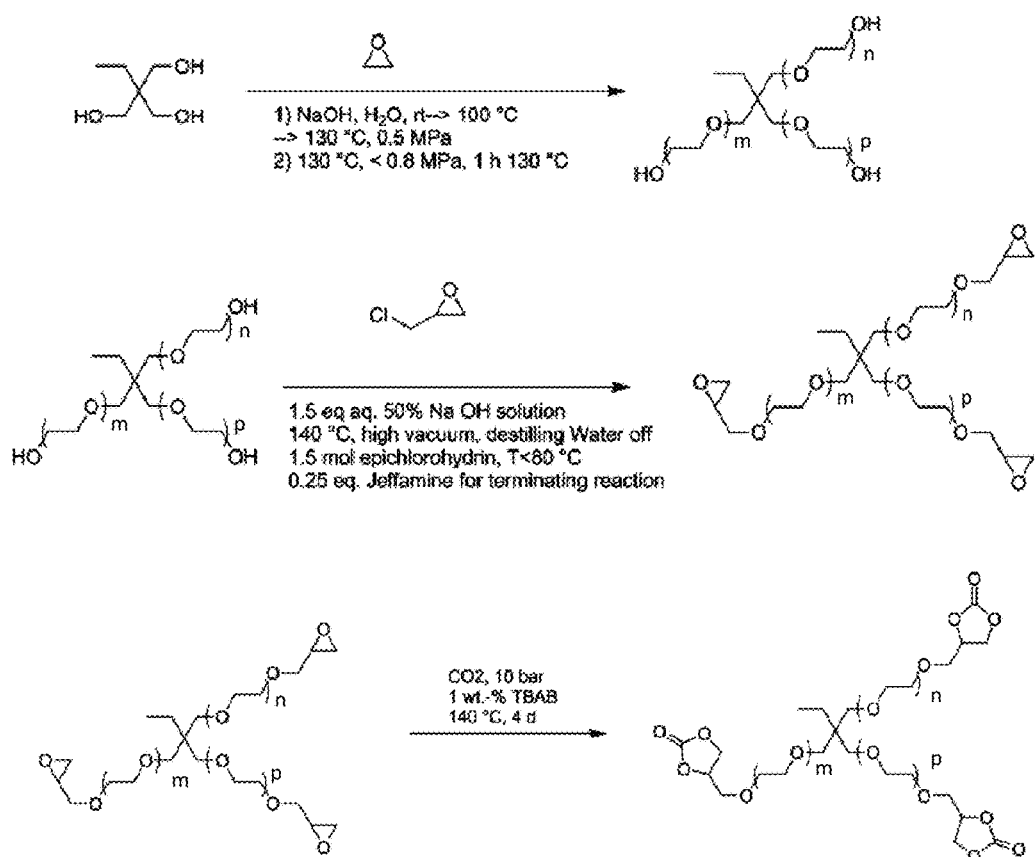
FIG. 5 shows the synthesis of ethoxylated trimethylolpropaneglycidylether carbonate of formula (IIb).

NIPU foams according to the invention were prepared in 400 g scale according to the procedure shown in FIG. 4 by using the same ingredients in the same amounts as described in Example 1, sample 3. The polymeric reaction turned out to be highly exothermic. Therefore, a foam mold (alumina: 1 cm wall thickness; 25×25×25 cm, lid: 4 holes with a diameter of 4 mm) provided with external cooling by using an ice water bath in order to maintain the temperature of the reacting mixture between 20 and 25° C. In addition, mixing times after adding HMDA were shortened (at most 5 minutes).

The foam mold was preheated at 80° C. and removed from the oven at different times before pouring the resin into it.

With decreasing mixing time and therefore decreasing viscosity of the composition, stronger foaming could be observed. With the longest mixing time of 6 min, only 2 cm foam height could be achieved (sample 1). Reducing the mixing time to 4 min yielded in 8 cm foam height at equal area. The temperature of the mold was qualitatively varied by removing the mold out of the oven at different times before pouring. If the mold is too hot ($t_{mold}$=0 min, direct at pouring, 80° C., sample 2), Solkane evaporated rapidly during pouring yielding big pores at the bottom of the foam and in small inhomogeneity. Nearly perfect foam formation with perfect homogeneity of pore (size) was achieved with 4 min mixing and a slightly warm mold ($t_{mold}$=4 min, approximately 50° C., sample 3). After curing for 14 h at 80° C. all samples showed no plane and smooth surface.

Densities were calculated by measuring the weight and the geometry of prepared cuboid samples (see Table 2). The densities ($\rho_{foam}$) were in the range of 0.140 g cm$^{-3}$ (sample 20) and 0.219 g cm$^{-3}$ (sample 18). Compared to standard PU foam (250913-8, I-70, soft foam) supplied by Faurecia with a density of 0.05 g cm$^{-3}$ our NIPU foams still need improvement regarding the foaming process. Pore sizes as measured by optical microscopy were in the range of 250 μm.

TABLE 2

| Sample | $t_{mixing}$ (min) | $t_{mold}$ (min) | Homogenous foam? | Foam height (cm) | $\rho_{foam}$ (g cm$^{-3}$) |
|---|---|---|---|---|---|
| 1 | 6 | 6 | yes | 2 | 0.219 |
| 2 | 5 | 0 | no | 7.5 | 0.167 |
| 3 | 4 | 4 | yes | 8 | 0.140 |

Therefore, it was possible to prepare flexible NIPU foam by using Solkane as blowing agent and a mixture of TMPGC and ETPMGC as cyclic carbonate component. The method of the invention makes it possible to prepare flexible and soft 100% biobased NIPU foam with comparable pore sizes to standard PU foams and with densities of 0.140 g cm$^{-3}$.

The invention claimed is:

1. A curable isocyanate free formulation for preparing a polyurethane foam comprising the following compounds:

Compound A chosen from multifunctional cyclic carbonates of formula (I) or a mixture thereof:

$$R^1 \!-\!\!\left(\!\!\left(\!\!O\!\!\right)\!\!-\!\!O\!\!-\!\!\!\overset{O}{\underset{O}{\bigcirc}}\!\!\right)_{\!\!i}$$ Formula (I)

wherein:
i is an integer from 2 to 10,
R$^1$ is a linear or branched hydrocarbon chain one or several carbon atoms of which may be replaced with an heteroatom, a cycloalkyl, an heterocycle, an aryl or an heteroaryl, said hydrocarbon chain having from 3 to 60 carbon atoms, Compound B chosen from multifunctional cyclic carbonates containing oxyalkylene groups —OR$^3$— of formula (II), except polypropylene oxide bis-carbonate, or a mixture thereof:

$$R^{1'}\!-\!\!\left(\!\!\left(\!\!OR^3\!\!\right)_{\!\!j}\!\!-\!\!O\!\!-\!\!\!\overset{O}{\underset{O}{\bigcirc}}\!\!\right)_{\!\!i'}$$ Formula (II)

wherein:
i' is an integer from 2 to 10,
R$^{1'}$ is a linear or branched hydrocarbon chain one or several carbon atoms of which may be replaced with an heteroatom, a cycloalkyl, an heterocycle, an aryl or an heteroaryl, said hydrocarbon chain having from 3 to 60 carbon atoms,
j is an integer from 1 to 10,
R$_3$ is a linear or branched hydrocarbon chain having from 2 to 6 carbon atoms, Compound C chosen from multifunctional amines of formula (III) or a mixture thereof:

$$R^2\!\!-\!\!(NH_2)_k$$ Formula (III)

wherein:
k is an integer from 2 to 6,
R$^2$ is a linear or branched hydrocarbon chain one or several carbon atoms of which may be replaced with an heteroatom, a cycloalkyl or an heterocycle, said hydrocarbon chain having from 2 to 60 carbon atoms, Compound D chosen from non-reactive blowing agents.

2. The curable isocyanate free formulation according to claim 1, wherein R$^1$ and R$^{1'}$, identical or different, are a linear or branched hydrocarbon chain having 3 to 10 carbon atoms.

3. The curable isocyanate free formulation according to claim 1, wherein i and i', identical or different, are integers from 2 to 6.

4. The curable isocyanate free formulation according to claim 1, wherein:

Compound A is chosen from a compound of formula (Ia):

(Ia)

[structure]

Compound B is chosen from compounds of formula (IIa) or a mixture thereof:

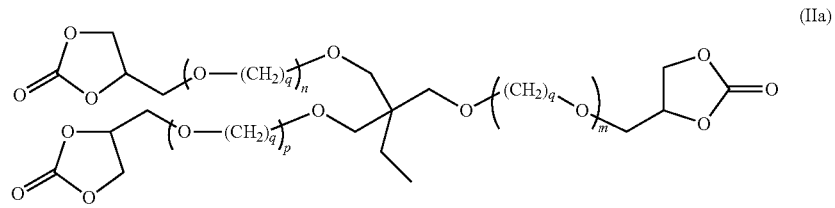

(IIa)

wherein:
q represents an integer from 2 to 20 and
n, m and p, identical or different, represent integers from 1 to 20.

5. The curable isocyanate free formulation according to claim 4, wherein:
Compound A is chosen from a compound of formula (Ia)
Compound B is chosen from a compound of formula (IIa) or a mixture thereof wherein q =2 and n, m, and p are 6 or 7.

6. The curable isocyanate free formulation according to claim 1, wherein the Compound C is chosen from 1,2-diamonethane, 1,3-diaminopropane, butane-1,4-diamine, pentane-1,5-diamine, 1,6-diaminohexane, 1,12 diaminododecane, isophorondiamine, polyethylene imine or dimeric fatty acid diamines.

7. The curable isocyanate free formulation according to claim 1, wherein compound D is chosen from liquids which boiling point is below 100° C., hydrocarbons, ethers, halogenated hydrocarbons, nitriles, nitrogen or carbon dioxide, or mixtures thereof.

8. The curable isocyanate free formulation according to claim 1, further comprising a catalyst as compound E.

9. A process for preparing a flexible non-isocyanate polyurethane foam comprising the steps of:
reacting compounds A and B with compound C in the presence of compound D and a catalyst as compound E so as to form an expanded reaction mixture,
curing said expanded reaction mixture so as to form a flexible non-isocyanate polyurethane foam,
wherein compounds A, B, C, and D comprise the curable isocyanate free formulation defined in claim 1.

10. The process according to claim 9, wherein:
compounds A and B are first mixed with compound E and compound C, so as to form a reaction mixture and start the polymerization of said reaction mixture,
then compound D is added to this reaction mixture.

11. A foamable system comprising:
a first part A containing:
Compound A which is chosen from multifunctional cyclic carbonates of formula (I) or a mixture thereof:

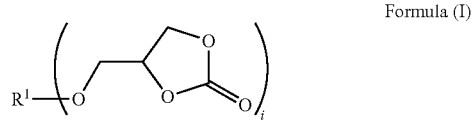

Formula (I)

wherein:
i is an integer from 2 to 10,
$R^1$ is a linear or branched hydrocarbon chain one or several carbon atoms of which may be replaced with an heteroatom, a cycloalkyl, an heterocycle, an aryl or an heteroaryl, said hydrocarbon chain having from 3 to 60 carbon atoms,
Compound B which is chosen from multifunctional cyclic carbonates containing oxyalkylene groups $—OR^3—$ of formula (II), except polypropylene oxide bis-carbonate, or a mixture thereof:

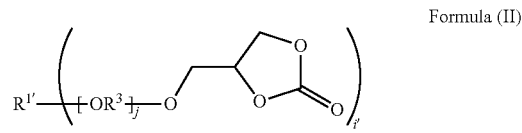

Formula (II)

wherein:
i' is an integer from 2 to 10,
$R^{1'}$ a linear or branched hydrocarbon chain one or several carbon atoms of which may be replaced with an heteroatom, a cycloalkyl, an heterocycle, an aryl or an heteroaryl, said hydrocarbon chain having from 3 to 60 carbon atoms,
j is an integer from 1 to 10,
$R^3$ is a linear or branched hydrocarbon chain having from 2 to 6 carbon atoms,
a second part B containing compound C chosen from multifunctional amines of formula (III) or a mixture thereof:

Formula (III)

wherein:
k is an integer from 2 to 6,
$R^2$ is a linear or branched hydrocarbon chain one or several carbon atoms of which may be replaced with an heteroatom, a cycloalkyl or an heterocycle, said hydrocarbon chain having from 2 to 60 carbon atoms.

12. The foamable system according to claim 11, further comprising a catalyst as compound E either in part A or in part B, or in a third part C preferably physically separated from part A and part B.

13. The foamable system according to claim 11, further comprising a non-reactive blowing agent as compound D either in part A, in part B or in third part C, or in a fourth part D preferably physically separated from part A, part B and part C.

14. The curable isocyanate free formulation according to claim 8, wherein the catalyst as compound E is chosen from amine catalysts or organometallic catalysts or mixtures thereof.

15. The foamable system of claim 11, wherein part A and part B are physically separated.

* * * * *